United States Patent
Smith-Simpson et al.

(10) Patent No.: US 9,691,029 B2
(45) Date of Patent: Jun. 27, 2017

(54) METHODS FOR PREDICTING AGE-OR DEVELOPMENTAL STAGE-APPROPRIATE FOODS FOR CHILDREN

(71) Applicant: NESTEC S.A., Vevey (CH)

(72) Inventors: Sarah Elizabeth Smith-Simpson, Rockford, MI (US); Anne McCandlish Emenhiser, Fremont, MI (US); Mary Michele Foley, Whitehall, MI (US)

(73) Assignee: Nestec S.A., Vevey (CH)

( * ) Notice: Subject to any disclaimer, the term of this patent is extended or adjusted under 35 U.S.C. 154(b) by 357 days.

(21) Appl. No.: 14/363,797

(22) PCT Filed: Dec. 14, 2012

(86) PCT No.: PCT/EP2012/075483
§ 371 (c)(1),
(2) Date: Jun. 8, 2014

(87) PCT Pub. No.: WO2013/087810
PCT Pub. Date: Jun. 20, 2013

(65) Prior Publication Data
US 2014/0372357 A1    Dec. 18, 2014

Related U.S. Application Data

(60) Provisional application No. 61/570,657, filed on Dec. 14, 2011.

(51) Int. Cl.
*G06F 17/00* (2006.01)
*G06N 5/02* (2006.01)
(Continued)

(52) U.S. Cl.
CPC ............... *G06N 5/04* (2013.01); *G01N 33/02* (2013.01); *G06Q 30/0241* (2013.01)

(58) Field of Classification Search
None
See application file for complete search history.

(56) References Cited

U.S. PATENT DOCUMENTS

2012/0031805 A1* 2/2012 Stolarczyk ............ A47J 39/006
                                                        206/541
2013/0079276 A1* 3/2013 Van Goudoever ..... A61K 38/16
                                                         514/4.8

FOREIGN PATENT DOCUMENTS

| EP | 0109965 | 6/1984 |
|---|---|---|
| EP | 1777173 | 4/2007 |
| WO | 90/08705 | 8/1990 |

OTHER PUBLICATIONS

Chen et al. "Age Appropriate Hedonic Scales to Measure Food Preferences of Young Children", Journal of Sensory Studies 11 (1996) 141-163.*

(Continued)

*Primary Examiner* — Li-Wu Chang
(74) *Attorney, Agent, or Firm* — Gary M. Lobel, Esq.

(57) ABSTRACT

The present disclosure provides methods for classifying food products and predicting appropriate ages and/or developmental stages that children should be provided with certain food products. In an embodiment, the methods include mathematical models that use the measurements of key texture attributes to predict the minimum age and/or developmental stage of food products. Using the methods of the present disclosure, classification of food products can be directed during early product development. Additionally, the methods of the present disclosure have generated an understanding of which key texture attributes differentiate appropriate products across developmental stages.

20 Claims, 1 Drawing Sheet

(51) Int. Cl.
*G06N 5/04* (2006.01)
*G06Q 30/02* (2012.01)
*G01N 33/02* (2006.01)

(56) References Cited

OTHER PUBLICATIONS

Carruth et al. "Prevalence of Picky Eaters among Infants and Toddlers and Their Caregivers' Decisions about Offering a New Food", Journal of the American Dietetic Association, pp. 57-64.*
Gaines et al. "How to Market & Sell a New Food Product to Grocery Stores", Nov. 1, 2011, pp. 1, https://web.archive.org/web/20111101205733/http://smallbusiness.chron.com/market-sell-new-food-product-grocery-stores-10795.html.*
Chapin et al. "Nonfatal Choking on Food Among Children 14 Years or Younger in the United States, 2001-2009", Pediatrics vol. 132, No. 2, Aug. 2013, pp. 275-281.*
Szczesniak "Texture is a sensory property", Food Quality and Preference 13(2002), pp. 215-225.*
Gisel "Effect of Food Texture on the Development of Chewing of Children Between Six Months and Two Years of Age", J. DMCN, 1991, pp. 69-79.*

* cited by examiner

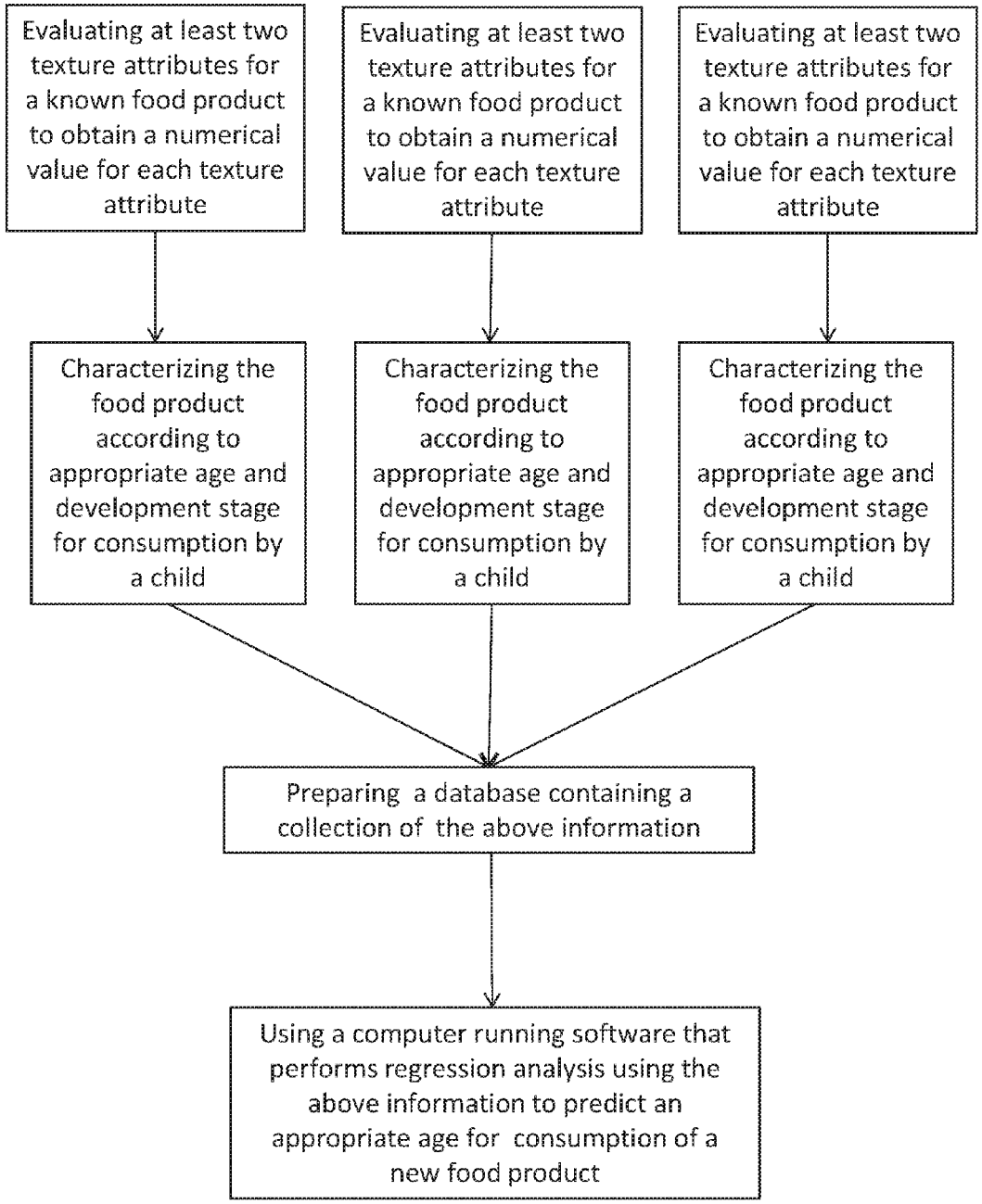

METHODS FOR PREDICTING AGE-OR DEVELOPMENTAL STAGE-APPROPRIATE FOODS FOR CHILDREN

BACKGROUND

The present disclosure relates generally to health and nutrition. More specifically, the present disclosure relates to methods for classifying food products and predicting appropriate ages and/or developmental stages that children should be provided with the food products.

It is known in the art that children of different ages and developmental stages present different levels of developmental skills including, for example, gross motor skills, fine motor skills, oral motor skills, and cognitive development. Indeed, from birth age to preschooler age, children develop at a rapid rate and are constantly fine tuning developmental skills as they age. Because an infant and a preschool-aged child have widely differing developmental skills, it is important for parents and caregivers to provide children with foods that are appropriate for the child's age and/or developmental stage. For example, an infant should not be provided with a hand-held biscuit for self-feeding because the infant has not yet refined her gross motor development to self-feed, nor would the infant be able to properly chew the biscuit in her mouth in order to swallow the biscuit. Alternatively, while a preschooler-aged child may be able to properly eat a hand-held biscuit, it is not likely that the biscuit is appropriate for the developmental stage of the older child.

It is not always easy, however, for parents and caregivers to determine appropriate foods for children. This is due, in part, to the fact that most parents simply are not experts in characterizing certain attributes of children's foods, or in immediately recognizing the child's appropriate developmental stage. As such, there exists a need to provide a comprehensive process for characterizing food products according to an appropriate age and/or developmental stage for a child to consume the food products. There also exists a need for an objective process for predicting an appropriate age and/or developmental stage at which a child can consume a food product.

SUMMARY

Methods for predicting an appropriate age or an appropriate developmental stage for a food product for a child are provided. Methods for classifying a food product in accordance with an appropriate age or an appropriate developmental stage of a child are also provided. In an embodiment, methods for predicting an appropriate age at which a child should be provided with a new food product are provided. The methods include evaluating at least two texture attributes of each of a plurality of known food products to obtain a numerical value for each texture attribute of each of the plurality of known food products, characterizing each of the plurality of known food products according to an appropriate age and an appropriate developmental stage for a child to consume the known food products, preparing a collection of information containing the plurality of known food products, the appropriate age for each known food product, the appropriate developmental stage for each known food product, and the textural attribute numerical values for each known food product, and using a computer running appropriate software to perform regression analysis using the collection of information to predict an appropriate age for the new food product (FIG. 1).

In an embodiment, the methods further include determining driving texture attributes from the at least two evaluated texture attributes.

In an embodiment, the evaluating is performed by a person by placing the known food products in the person's mouth.

In an embodiment, the evaluating is performed by an expert panel of at least two individuals.

In an embodiment, the evaluating is performed using machines.

In an embodiment, the at least two texture attributes are selected from the group consisting of amount of pieces in matrix, surface roughness, firmness, moistness, breakdown, cohesiveness of the mass, adhesiveness of the mass, moisture absorption, number of manipulations (to prepare to swallow), ease of swallow, residual mouthcoating, denseness, fracturability, roughness of the mass, force, work, and slope, length, width, thickness, moisture, Bostwick, and combinations thereof.

In an embodiment, the known food products are children's food products.

In an embodiment, the new food product is a children's food product.

In an embodiment, the known food products are one of snacks and meals.

In an embodiment, the collection of information is a database.

In an embodiment, the at least one of the plurality of known food products is a snack food product.

In an embodiment, the at least two texture attributes may include firmness and breakdown.

In an embodiment, at least one of the plurality of known food products is a meal food product.

In an embodiment, the at least two texture attributes may include residual mouthcoating and roughness of mass.

In another embodiment, methods for predicting an appropriate developmental stage at which a child should be provided with a new food product are provided. The methods include evaluating at least two texture attributes of each of a plurality of known food products to obtain a numerical value for each texture attribute of each of the plurality of known food products, characterizing each of the plurality of known food products according to an appropriate age and an appropriate developmental stage for a child to consume the known food products, preparing a collection of information containing the plurality of known food products, the appropriate age for each known food product, the appropriate developmental stage for each known food product, and the textural attribute numerical values for each known food product, and using a computer running appropriate software to perform discriminant analysis using the collection of information to predict an appropriate developmental stage for the new food product.

In an embodiment, the at least one of the plurality of known food products is a snack food product. The at least two texture attributes may include firmness, breakdown, ease of swallow and residual mouthcoating.

In an embodiment, the at least one of the plurality of known food products is a meal food product. The at least two texture attributes may include moistness, ease of swallow and denseness.

In yet another embodiment, methods for classifying a new food product with respect to an appropriate age at which a child should be provided with the new food product. The methods include evaluating at least two texture attributes of each of a plurality of known food products to obtain a numerical value for each texture attribute of each of the plurality of known food products, characterizing each of the plurality of known food products according to an appropriate age and an appropriate developmental stage for a child to consume the known food products, preparing a collection of information containing the plurality of known food products, the appropriate age for each known food product, the appropriate developmental stage for each known food product, and the textural attribute numerical values for each known food product, and using a computer running appropriate software to perform regression analysis using the collection of information to classify the new food product according to an appropriate age for the new food product.

In an embodiment, the at least one of the plurality of known food products is a snack food product. The at least two texture attributes may include firmness and breakdown.

In an embodiment, the at least one of the plurality of known food products is a meal food product. The at least two texture attributes may include residual mouthcoating, and roughness of mass.

In still yet another embodiment, methods for classifying a new food product with respect to an appropriate developmental stage at which a child should be provided with the new food product are provided. The methods include evaluating at least two texture attributes of each of a plurality of known food products to obtain a numerical value for each texture attribute of each of the plurality of known food products, characterizing each of the plurality of known food products according to an appropriate age and an appropriate developmental stage for a child to consume the known food products, preparing a collection of information containing the plurality of known food products, the appropriate age for each known food product, the appropriate developmental stage for each known food product, and the textural attribute numerical values for each known food product, and using a computer running appropriate software to perform discriminant analysis using the collection of information to classify the new food product according to an appropriate developmental stage for the new food product.

In an embodiment, the at least one of the plurality of known food products is a snack food product. The at least two texture attributes may include firmness, breakdown, ease of swallow and residual mouthcoating.

In an embodiment, the at least one of the plurality of known food products is a meal food product. The at least two texture attributes may include moistness, ease of swallow, denseness.

In yet another embodiment, methods for predicting an appropriate age for a child to consume a snack food product are provided. The methods include analyzing a firmness of the snack food product to obtain a firmness value, analyzing a breakdown of the snack food product to obtain a breakdown value, and calculating the appropriate age of the child by inserting the firmness value and the breakdown value into a formula, the formula being age=78.5−1.4*(firmness value)−0.4*(breakdown value)+0.0123*(firmness value).

In an embodiment, the step of analyzing a firmness of the snack food product is performed using a Chewing method.

In an embodiment, the step of analyzing a breakdown of the snack food product is performed using a Chewing method.

In an embodiment, the step of analyzing a firmness of the snack food product includes at least two analysis of the food product to obtain first and second firmness values, and wherein the firmness value is an average of the first and second firmness values.

In an embodiment, the step of analyzing a breakdown of the snack food product includes at least two analysis of the food product to obtain first and second breakdown values, and wherein the breakdown value is an average of the first and second breakdown values.

In an embodiment, the age is calculated in months.

In still yet another embodiment, methods for predicting an appropriate age for a child to consume a meal food product are provided. The methods include analyzing a residual mouthcoating of the meal food product to obtain a residual mouthcoating value, analyzing a roughness of mass of the meal food product to obtain a roughness of mass value, and calculating the appropriate age of the child by inserting the residual mouthcoating value and the roughness of mass value into a formula, the formula being age=2.45−0.11*(residual mouthcoating value)+0.50*(roughness of mass value).

In an embodiment, the step of analyzing a residual mouthcoating of the meal food product is performed using a Tongue to Palate method.

In an embodiment, the step of analyzing a roughness of mass of the meal food product is performed using a Chewing method.

In another embodiment, methods for predicting an appropriate age for a child to consume a new food product are provided. The methods include performing statistical analysis on a first set of numerical values describing at least two texture attributes of each of a plurality of known food products, identifying at least two driving texture attributes that are good predictors of age from the at least two texture attributes, the at least two driving texture attributes selected from the group consisting of firmness, breakdown, residual mouthcoating, roughness of mass, or combinations thereof, evaluating the new food product to obtain a second set of numerical values describing the at least two driving texture attributes, and using a computer running appropriate software to perform regression analysis using the second set of numerical values to predict the appropriate age.

In an embodiment, the new food product is a snack food product. The at least two driving texture attributes may be selected from the group consisting of firmness, breakdown, or combinations thereof.

In an embodiment, the firmness numerical value of the snack food product is obtained using a Chewing Method.

In an embodiment, the breakdown numerical value of the snack food product is obtained using a Chewing Method.

In an embodiment, the new food product is a meal food product. The at least two driving texture attributes may be selected from the group consisting of residual mouthcoating, roughness of mass, or combinations thereof.

In an embodiment, the residual mouthcoating numerical value of the meal food product is obtained using a Tongue to Palate Method.

In an embodiment, the roughness of mass numerical value of the meal food product is obtained using a Chewing Method.

In yet another embodiment, methods for predicting an appropriate developmental stage for a child to consume a snack food product are provided. The methods include performing statistical analysis on a first set of numerical values describing at least two texture attributes of each of a plurality of known food products, identifying at least two driving texture attributes that are good predictors of developmental stage from the at least two texture attributes, the at least two driving texture attributes selected from the group consisting of firmness, breakdown, ease of swallow, residual mouthcoating, or combinations thereof, evaluating the snack food product to obtain a second set of numerical values describing the at least two driving texture attributes, and using a computer running appropriate software to perform discriminant analysis using the second set of numerical values to predict the appropriate developmental stage.

In an embodiment, the firmness numerical value of the snack food product is obtained using a Chewing Method.

In an embodiment, the breakdown numerical value of the snack food product is obtained using a Chewing Method.

In an embodiment, the ease of swallow numerical value of the snack food product is obtained using a Tongue to Palate Method.

In an embodiment, the residual mouthcoating numerical value of the snack food product is obtained using a Tongue to Palate Method.

In still yet another embodiment, methods for predicting an appropriate developmental stage for a child to consume a meal food product are provided. The methods include performing statistical analysis on a first set of numerical values describing at least two texture attributes of each of a plurality of known food products, identifying at least two driving texture attributes that are good predictors of developmental stage from the at least two texture attributes, the at least two driving texture attributes selected from the group consisting of moistness, ease of swallow, denseness, or combinations thereof, evaluating the meal food product to obtain a second set of numerical values describing the at least two driving texture attributes, and using a computer running appropriate software to perform discriminant analysis using the second set of numerical values to predict the appropriate developmental stage.

In an embodiment, the moistness numerical value of the meal food product is obtained using a Tongue to Palate Method.

In an embodiment, the ease of swallow numerical value of the meal food product is obtained using a Tongue to Palate Method.

In an embodiment, the denseness numerical value of the meal food product is obtained using a Chewing Method.

In yet another embodiment, methods for classifying a snack food product with respect to an appropriate age for a child to consume the snack food product are provided. The methods include analyzing a firmness of the snack food product to obtain a firmness value, analyzing a breakdown of the snack food product to obtain a breakdown value, and classifying the snack food product based on the appropriate age of the child by inserting the firmness value and the breakdown value into a formula, the formula being age=78.5−1.4*(firmness value)−0.4*(breakdown value)+0.0123*(firmness value)$^2$.

In an embodiment, the step of analyzing a firmness of the snack food product is performed using a Chewing method.

In an embodiment, the step of analyzing a breakdown of the snack food product is performed using a Chewing method.

In an embodiment, the step of analyzing a firmness of the snack food product includes at least two analysis of the food product to obtain first and second firmness values, and wherein the firmness value is an average of the first and second firmness values.

In an embodiment, the step of analyzing a breakdown of the snack food product includes at least two analysis of the food product to obtain first and second breakdown values, and wherein the breakdown value is an average of the first and second breakdown values.

In an embodiment, the age is calculated in months.

In still yet another embodiment, methods for classifying a meal food product with respect to an appropriate age for a child to consume the meal food product are provided. The methods include analyzing a residual mouthcoating of the meal food product to obtain a residual mouthcoating value, analyzing a roughness of mass of the meal food product to obtain a roughness of mass value, and classifying the meal food product based on the appropriate age of the child by inserting the residual mouthcoating value and the roughness of mass value into a formula, the formula being age=2.45−0.11*(residual mouthcoating value)+0.50*(roughness of mass value).

In an embodiment, the step of analyzing a residual mouthcoating of the meal food product is performed using a Tongue to Palate method.

In an embodiment, the step of analyzing a roughness of mass of the meal food product is performed using a Chewing method.

In an embodiment, the step of analyzing a residual mouthcoating of the meal food product includes at least two analysis of the food product to obtain first and second residual mouthcoating values, and wherein the residual mouthcoating value is an average of the first and second residual mouthcoating values.

In an embodiment, the step of analyzing a roughness of mass of the meal food product includes at least two analysis of the food product to obtain first and second roughness of mass values, and wherein the roughness of mass value is an average of the first and second roughness of mass values.

In an embodiment, the age is calculated in months.

In another embodiment, methods for classifying a new food product with respect to an appropriate age for a child to consume the new food product are provided. The methods include performing statistical analysis on a first set of numerical values describing at least two texture attributes of each of a plurality of known food products, identifying at least two driving texture attributes that are good predictors of age from the at least two texture attributes, the at least two driving texture attributes selected from the group consisting of firmness, breakdown, residual mouthcoating, roughness of mass, or combinations thereof, evaluating the new food product to obtain a second set of numerical values describing the at least two driving texture attributes, and using a computer running appropriate software to perform regression analysis using the second set of numerical values to predict the appropriate age.

In an embodiment, the new food product is a snack food product. The at least two driving texture attributes may be selected from the group consisting of firmness, breakdown, or combinations thereof.

In an embodiment, the firmness numerical value of the snack food product is obtained using a Chewing Method.

In an embodiment, the breakdown numerical value of the snack food product is obtained using a Chewing Method.

In an embodiment, the new food product is a meal food product. The at least two driving texture attributes may be selected from the group consisting of residual mouthcoating, roughness of mass, or combinations thereof.

In an embodiment, the residual mouthcoating numerical value of the meal food product is obtained using a Tongue to Palate Method.

In an embodiment, the roughness of mass numerical value of the meal food product is obtained using a Chewing Method.

In another embodiment, methods for classifying a snack food product with respect to an appropriate developmental stage for a child to consume the snack food product are provided. The methods include performing statistical analysis on a first set of numerical values describing at least two texture attributes of each of a plurality of known food products, identifying at least two driving texture attributes that are good predictors of developmental stage from the at least two texture attributes, the at least two driving texture attributes selected from the group consisting of firmness, breakdown, ease of swallow, residual mouthcoating, or combinations thereof, evaluating the snack food product to obtain a second set of numerical values describing the at least two driving texture attributes, and using a computer running appropriate software to perform discriminant analysis using the second set of numerical values to predict the appropriate developmental stage.

In an embodiment, the firmness numerical value of the snack food product is obtained using a Chewing Method.

In an embodiment, the breakdown numerical value of the snack food product is obtained using a Chewing Method.

In an embodiment, the ease of swallow numerical value of the snack food product is obtained using a Tongue to Palate Method.

In an embodiment, the residual mouthcoating numerical value of the snack food product is obtained using a Tongue to Palate Method.

In still yet another embodiment, methods for classifying a meal food product with respect to an appropriate developmental stage for a child to consume the meal food product are provided. The methods include performing statistical analysis on a first set of numerical values describing at least two texture attributes of each of a plurality of known food products, identifying at least two driving texture attributes that are good predictors of developmental stage from the at least two texture attributes, the at least two driving texture attributes selected from the group consisting of moistness, ease of swallow, denseness, or combinations thereof, evaluating the meal food product to obtain a second set of numerical values describing the at least two driving texture attributes, and using a computer running appropriate software to perform discriminant analysis using the second set of numerical values to predict the appropriate developmental stage.

In an embodiment, the moistness numerical value of the meal food product is obtained using a Tongue to Palate Method.

In an embodiment, the ease of swallow numerical value of the meal food product is obtained using a Tongue to Palate Method.

In an embodiment, the denseness numerical value of the meal food product is obtained using a Chewing Method.

In yet another embodiment, methods for reducing the risk of a child choking on a snack food product are provided. The methods include providing a snack food product characterized as appropriate for a child of a predetermined age, the characterizing including analyzing a firmness of the snack food product to obtain a firmness value, analyzing a breakdown of the snack food product to obtain a breakdown value, and calculating the predetermined age of the child by inserting the firmness value and the breakdown value into a formula, the formula being age=78.5−1.4*(firmness value)−0.4*(breakdown value)+0.0123*(firmness value); and instructing a parent or caregiver to administer the snack food product to the child.

In an embodiment, the step of analyzing a firmness of the snack food product is performed using a Chewing Method.

In an embodiment, the step of analyzing a breakdown of the snack food product is performed using a Chewing Method.

In an embodiment, the step of analyzing a firmness of the snack food product includes at least two analysis of the food product to obtain first and second firmness values, and wherein the firmness value is an average of the first and second firmness values.

In an embodiment, the step of analyzing a breakdown of the snack food product includes at least two analysis of the food product to obtain first and second breakdown values, and wherein the breakdown value is an average of the first and second breakdown values.

In an embodiment, the age is calculated in months.

In yet another embodiment, methods for reducing the risk of a child choking on a meal food product are provided. The methods include providing a meal food product characterized as appropriate for a child of a predetermined age, the characterizing including analyzing a residual mouthcoating of the meal food product to obtain a residual mouthcoating value, analyzing a roughness of mass of the meal food product to obtain a roughness of mass value, and calculating the predetermined age of the child by inserting the residual mouthcoating value and the roughness of mass value into a formula, the formula being age=2.45−0.11*(residual mouthcoating value)+0.50*(roughness of mass value); and instructing a parent or caregiver to administer the meal food product to the child.

In an embodiment, the step of analyzing a residual mouthcoating of the meal food product is performed using a Tongue to Palate Method.

In an embodiment, the step of analyzing a roughness of mass of the meal food product is performed using a Chewing Method.

In an embodiment, the step of analyzing a residual mouthcoating of the meal food product includes at least two analysis of the food product to obtain first and second residual mouthcoating values, and wherein the residual mouthcoating value is an average of the first and second residual mouthcoating values.

In an embodiment, the step of analyzing a roughness of mass of the meal food product includes at least two analysis of the food product to obtain first and second roughness of mass values, and wherein the roughness of mass value is an average of the first and second roughness of mass values.

In an embodiment, the age is calculated in months.

In another embodiment, methods for training an individual to predict an appropriate age for a child to consume a snack food product are provided. The methods include instructing the individual to analyze a firmness of the snack food product to obtain a firmness value, instructing the individual to analyze a breakdown of the snack food product to obtain a breakdown value, calculating the appropriate age of the child by inserting the firmness value and the breakdown value into a formula, the formula being age=78.5−1.4*(firmness value)−0.4*(breakdown value)+0.0123*(firmness value)$^2$, and comparing the calculated age to a known age.

In an embodiment, the known age is obtained from a database of information.

In an embodiment, the step of analyzing a firmness of the snack food product is performed using a Chewing method.

In an embodiment, the step of analyzing a breakdown of the snack food product is performed using a Chewing method.

In an embodiment, the age is calculated in months.

In yet another embodiment, methods for training an individual to predict an appropriate age for a child to consume a meal food product are provided. The methods include instructing the individual to analyze a residual mouthcoating of the meal food product to obtain a residual mouthcoating value, instructing the individual to analyze a roughness of mass of the meal food product to obtain a roughness of mass value, calculating the appropriate age of the child by inserting the residual mouthcoating value and the roughness of mass value into a formula, the formula being age=2.45−0.11*(residual mouthcoating value)+0.50* (roughness of mass value), and comparing the calculated age to a known age.

In an embodiment, the known age is obtained from a database of information.

In an embodiment, the step of analyzing a residual mouthcoating of the meal food product is performed using a Tongue to Palate method.

In an embodiment, the step of analyzing a roughness of mass of the meal food product is performed using a Chewing method.

In an embodiment, the age is calculated in months.

In still yet another embodiment, methods for training an individual to predict an appropriate developmental stage for a child to consume a snack food product are provided. The methods include instructing the individual to analyze texture attributes of firmness, breakdown, ease of swallow and residual mouthcoating of a known snack food product, providing a database including a plurality of known texture attribute values for each of a plurality of known food products, the database further including an appropriate developmental stage for each of the plurality of known food products, and the plurality of known food products including the known snack food product, using discriminant analysis to determine probabilities of the known snack food product being classified into each of a plurality of development stages, and comparing the probabilities with the known appropriate developmental stage of the known snack food product.

In an embodiment, the firmness numerical value of the snack food product is obtained using a Chewing Method.

In an embodiment, the breakdown numerical value of the snack food product is obtained using a Chewing Method.

In an embodiment, the ease of swallow numerical value of the snack food product is obtained using a Tongue to Palate Method.

In an embodiment, the residual mouthcoating numerical value of the snack food product is obtained using a Tongue to Palate Method.

In yet another embodiment, methods for training an individual to predict an appropriate stage for a child to consume a meal food product are provided. The methods include instructing the individual to analyze texture attributes of moistness, ease of swallow and denseness of a known meal food product, providing a database including a plurality of known texture attribute values for each of a plurality of known food products, the database further including an appropriate developmental stage for each of the plurality of known food products, and the plurality of known food products including the known meal food product, using discriminant analysis to determine probabilities of the known meal food product being classified into each of a plurality of development stages, and comparing the probabilities with the known appropriate developmental stage of the known meal food product.

In an embodiment, the moistness numerical value of the meal food product is obtained using a Tongue to Palate Method.

In an embodiment, the ease of swallow numerical value of the meal food product is obtained using a Tongue to Palate Method.

In an embodiment, the denseness numerical value of the meal food product is obtained using a Chewing Method.

In yet another embodiment, new food products that have been modified or designed using a method for evaluating at least two texture attributes of the product are provided. The method includes evaluating at least two texture attributes of each of a plurality of known food products to obtain a numerical value for each texture attribute of each of the plurality of known food products, characterizing each of the plurality of known food products according to an appropriate age and an appropriate developmental stage for a child to consume the known food products, preparing a collection of information containing the plurality of known food products, the appropriate age for each known food product, the appropriate developmental stage for each known food product, and the texture attribute numerical values for each known food product, evaluating at least two texture attributes of a new food product to obtain a numerical value for each texture attribute, and using a computer running appropriate software to perform regression analysis using the collection of information to predict an appropriate age for the new food product. The method further includes modifying or designing the new food product according to the predicted appropriate age.

In still yet another embodiment, new food products that have been modified or designed using a method for evaluating at least two texture attributes of the product are provided. The method for evaluating includes evaluating at least two texture attributes of each of a plurality of known food products to obtain a numerical value for each texture attribute of each of the plurality of known food products, characterizing each of the plurality of known food products according to an appropriate age and an appropriate developmental stage for a child to consume the known food products, preparing a collection of information containing the plurality of known food products, the appropriate age for each known food product, the appropriate developmental stage for each known food product, and the texture attribute numerical values for each known food product, evaluating at least two texture attributes of a new food product to obtain a numerical value for each texture attribute, and using a computer running appropriate software to perform discriminant analysis using the collection of information to predict an appropriate developmental stage for the new food product. The method further includes modifying or designing the new food product according to the predicted developmental stage.

In another embodiment, methods for selling or offering for sale a new food product are provided. The methods include preparing a new food product using a method for evaluating at least two texture attributes of the product, and selling or offering for sale the new food product. The method for evaluating includes evaluating at least two texture attributes of each of a plurality of known food products to obtain a numerical value for each texture attribute of each of the plurality of known food products, characterizing each of the plurality of known food products according to an appropriate age and an appropriate developmental stage for a child to consume the known food products, preparing a collection of information containing the plurality of known food products, the appropriate age for each known food product, the appropriate developmental stage for each known food product, and the texture attribute numerical values for each known food product, evaluating at least two texture attributes of a new food product to obtain a numerical value for each texture attribute, using a computer running appropriate software to perform regression analysis using the collection of information to predict an appropriate age for the new food product, and preparing the new food product according to the predicted appropriate age.

In yet another embodiment, methods for selling or offering for sale a new food product are provided. The methods include preparing a new food product using a method for evaluating at least two texture attributes of the product and selling or offering for sale the new food product. The methods for evaluating include evaluating at least two texture attributes of each of a plurality of known food products to obtain a numerical value for each texture attribute of each of the plurality of known food products, characterizing each of the plurality of known food products according to an appropriate age and an appropriate developmental stage for a child to consume the known food products, preparing a collection of information containing the plurality of known food products, the appropriate age for each known food product, the appropriate developmental stage for each known food product, and the texture attribute numerical values for each known food product, evaluating at least two texture attributes of a new food product to obtain a numerical value for each texture attribute, using a computer running appropriate software to perform discriminant analysis using the collection of information to predict an appropriate developmental stage for the new food product, and preparing the new food product according to the predicted developmental stage.

In another embodiment, methods for selling or offering for sale a new food product are provided. The methods include modifying or designing a new food product using a method for evaluating at least two texture attributes of the product, and selling or offering for sale the new food product. The methods for evaluating include evaluating at least two texture attributes of each of a plurality of known food products to obtain a numerical value for each texture attribute of each of the plurality of known food products, characterizing each of the plurality of known food products according to an appropriate age and an appropriate developmental stage for a child to consume the known food products, preparing a collection of information containing the plurality of known food products, the appropriate age for each known food product, the appropriate developmental stage for each known food product, and the texture attribute numerical values for each known food product, evaluating at least two texture attributes of a new food product to obtain a numerical value for each texture attribute, using a computer running appropriate software to perform regression analysis using the collection of information to predict an appropriate age for the new food product, and modifying or designing the new food product according to the predicted appropriate age.

In still yet another embodiment, methods for selling or offering for sale a new food product are provided. The methods include modifying or designing a new food product using a method for evaluating at least two texture attributes of the product, and selling or offering for sale the new food product. The methods for evaluating include evaluating at least two texture attributes of each of a plurality of known food products to obtain a numerical value for each texture attribute of each of the plurality of known food products, characterizing each of the plurality of known food products according to an appropriate age and an appropriate developmental stage for a child to consume the known food products, preparing a collection of information containing the plurality of known food products, the appropriate age for each known food product, the appropriate developmental stage for each known food product, and the texture attribute numerical values for each known food product, evaluating at least two texture attributes of a new food product to obtain a numerical value for each texture attribute, using a computer running appropriate software to perform discriminant analysis using the collection of information to predict an appropriate developmental stage for the new food product, and modifying or designing the new food product according to the predicted developmental stage.

In yet another embodiment, methods for marketing a new food product, are provided. The methods include preparing a new food product using a method for evaluating at least two texture attributes of the product, and marketing the new food product. The methods for evaluating include evaluating at least two texture attributes of each of a plurality of known food products to obtain a numerical value for each texture attribute of each of the plurality of known food products, characterizing each of the plurality of known food products according to an appropriate age and an appropriate developmental stage for a child to consume the known food products, preparing a collection of information containing the plurality of known food products, the appropriate age for each known food product, the appropriate developmental stage for each known food product, and the texture attribute numerical values for each known food product, evaluating at least two texture attributes of a new food product to obtain a numerical value for each texture attribute, using a computer running appropriate software to perform regression analysis using the collection of information to predict an appropriate age for the new food product, and preparing the new food product according to the predicted appropriate age.

In yet another embodiment, methods for marketing a new food product are provided. The methods include preparing a new food product using a method for evaluating at least two texture attributes of the product, and marketing the new food product. The methods for evaluating include evaluating at least two texture attributes of each of a plurality of known food products to obtain a numerical value for each texture attribute of each of the plurality of known food products, characterizing each of the plurality of known food products according to an appropriate age and an appropriate developmental stage for a child to consume the known food products, preparing a collection of information containing the plurality of known food products, the appropriate age for each known food product, the appropriate developmental stage for each known food product, and the texture attribute numerical values for each known food product, evaluating at least two texture attributes of a new food product to obtain a numerical value for each texture attribute, using a computer running appropriate software to perform discriminant analysis using the collection of information to predict an appropriate developmental stage for the new food product, and preparing the new food product according to the predicted developmental stage.

In still yet another embodiment, methods for marketing a new food product are provided. The methods include modifying or designing a new food product using a method for evaluating at least two texture attributes of the product, and marketing the new food product. The methods for evaluating include evaluating at least two texture attributes of each of a plurality of known food products to obtain a numerical value for each texture attribute of each of the plurality of known food products, characterizing each of the plurality of known food products according to an appropriate age and an appropriate developmental stage for a child to consume the known food products, preparing a collection of information containing the plurality of known food products, the appropriate age for each known food product, the appropriate developmental stage for each known food product, and the texture attribute numerical values for each known food product, evaluating at least two texture attributes of a new food product to obtain a numerical value for each texture attribute, using a computer running appropriate software to perform regression analysis using the collection of information to predict an appropriate age for the new food product, and modifying or designing the new food product according to the predicted appropriate age.

In yet another embodiment, methods for marketing a new food product are provided. The methods include modifying or designing a new food product using a method for evaluating at least two texture attributes of the product, and marketing the new food product. The methods for evaluating include evaluating at least two texture attributes of each of a plurality of known food products to obtain a numerical value for each texture attribute of each of the plurality of known food products, characterizing each of the plurality of known food products according to an appropriate age and an appropriate developmental stage for a child to consume the known food products, preparing a collection of information containing the plurality of known food products, the appropriate age for each known food product, the appropriate developmental stage for each known food product, and the texture attribute numerical values for each known food product, evaluating at least two texture attributes of a new food product to obtain a numerical value for each texture attribute, using a computer running appropriate software to perform discriminant analysis using the collection of information to predict an appropriate developmental stage for the new food product, and modifying or designing the new food product according to the predicted developmental stage.

An advantage of the present disclosure is to provide methods for predicting an appropriate age for a child to consume a food product.

Another advantage of the present disclosure is to provide methods for predicting an appropriate developmental stage for a child to consume a food product.

Yet another advantage of the present disclosure is to provide methods for classifying food products according to a child's age.

Still yet another advantage of the present disclosure is to provide methods for classifying food products according to a child's developmental stage.

Another advantage of the present disclosure is to provide methods for reducing the risk of choking by providing a child with an age- and/or developmental stage-appropriate food product.

Yet another advantage is to provide methods for training expert panels how to classify food products according to a child's appropriate age- and/or developmental stage.

Additional features and advantages are described herein, and will be apparent from the following Detailed Description.

BRIEF DESCRIPTION OF THE DRAWINGS

FIG. 1 contains a flow chart illustrating one embodiment of the method of the present disclosure.

DETAILED DESCRIPTION

As used in this disclosure and the appended claims, the singular forms "a," "an" and "the" include plural referents unless the context clearly dictates otherwise.

As used herein, "about" is understood to refer to numbers in a range of numerals. Moreover, all numerical ranges herein should be understood to include all integer, whole or fractions, within the range.

As used herein, "Chewing Method" refers to a method of evaluating a food product comprising compressing and chewing a food sample with the molars. The primary parameters assessed in the Chewing Method include, but are not limited to, first bite with molars, first chew with molars, and chewing the sample 5-7 times with molars.

As used herein, "developmental stage(s)" refers to a stage in a child's life where children typically begin to exhibit certain behaviors or are typically capable of performing certain actions. For example, solid foods are typically introduced to a child in a "Supported Sitter" stage, which may be from about four to about six months of age. Other examples of developmental stages include "Birth+" at about zero to about four months, "Sitter" at about six+ months, "Crawler" at about eight+ months, "Crawler 10+" at about 10 months, "Toddler" at about twelve+ months, and "Preschooler" at about 24+ months.

As used herein, "discriminant analysis" refers to linear discriminant analysis, which is a method used in statistics, pattern recognition and machine learning to find a linear combination of features that characterizes or separates two or more classes of objects or events. The skilled artisan will immediately appreciate what is meant by discriminant analysis and will be able to use discriminant analysis to find a good predictor for a class y of any sample of the same distribution given a set of observations $\vec{x}$ for each sample of an object or event with a known classy.

As used herein, "driving texture attribute" or "key texture attribute" refers to a texture attribute that has a significant impact on distinguishing a food product as being appropriately classified for a particular age or a particular developmental stage. A driving texture attribute may be identified by statistical analysis (e.g., stepwise linear regression analysis, stepwise discriminant analysis, etc.) of a much larger group of texture attributes.

As used herein, "meal" food product(s) refers to one or more food products intended to be consumed at normal meal times of breakfast, lunch and dinner.

As used herein, "regression analysis" refers to a statistical analysis technique that includes many techniques for modeling and analyzing several variables, when the focus is on the relationship between a dependent variable and one or more independent variables. Regression analysis helps one understand how the typical value of the dependent variable changes when any one of the independent variables is varied, while the other independent variables are held fixed. The regression analysis may be any type of regression analysis and may be, for example, linear regression, or multiple linear regression, etc. The skilled artisan will immediate appreciate what is meant by regression analysis and will know how to use regression analysis to determine a relationship between a dependent variable and one or more independent variables.

As used herein, "snack" food product(s) refers to one or more food products that are typically smaller in portion size than a meal food product and/or are intended to be consumed between normal meals of breakfast, lunch and dinner.

As used herein, the phrase "texture attributes" refer to attributes or descriptive characteristics relating to the texture of a food product. Texture attributes may include, but are not limited to, amount of pieces in matrix, surface roughness, firmness, moistness, breakdown, cohesiveness of the mass, adhesiveness of the mass, moisture absorption, number of manipulations (to prepare to swallow), ease of swallow, residual mouthcoating, denseness, fracturability, and roughness of the mass. In an embodiment, the texture attributes of amount of pieces in matrix, surface roughness and number of manipulations (to prepare to swallow) may all be measured using the Tongue to Palate Method, as will be described herein below. In another embodiment, the texture attributes of denseness, fracturability and roughness of the mass may all be measured using the Chewing Method, as will be described herein below. Many of the above-mentioned texture attributes may also be measured using both the Tongue to Palate Method of evaluation as well as the Chewing Method. For example, an in an embodiment, firmness, moistness, moisture absorption, breakdown, cohesiveness of the mass, adhesiveness of the mass, ease of swallow, and residual mouthcoating are all examples of texture attributes that may be measured according to either or both of the Tongue to Palate Method or the Chewing Method.

As used herein, "Tongue to Palate Method" refers to a method of evaluating a food product comprising compressing and manipulating a food sample with the tongue against the hard palate. The primary parameters assessed in the Tongue to Palate Method include, but are not limited to, initial tongue manipulation, first compression with tongue to palate, manipulation of the sample 5-7 times with the tongue against the palate, and number of manipulations with the tongue.

In 2002, a Developmental Food Continuum was created by Dr. Kay Toomey, which outlines appropriate textures during transitions between textured food groups. Indeed, prior to the present disclosure, food products were evaluated by a limited number of internal and external experts who would subjectively evaluate prototypes of a new innovation product and use comparative analysis to suggest appropriate staging. While such subjective evaluation is useful, a method for objective, or a combination of subjective and objective, analysis would be more reliable.

Accordingly, the present disclosure is directed to a set of validated mathematical models which use the measurement of key texture attributes to predict the minimum age and developmental stage of food products. Specifically, the present disclosure is directed to identification of driving texture attributes that distinguish each stage within Applicant's children's foods portfolio and the creation of a mathematical model to predict appropriate staging with Applicant's Start Healthy Stay Healthy ("SHSH") Milestone Stage System for new products. Applicant's SHSH Milestone Stage System, a version of which is shown in Table 1 below, classifies the gross motor development, fine motor development, oral motor development, cognitive development and appropriate products for six different stages of child development including, for example, Birth+ (0-4 months), Supported Sitter (4-6 months), Sitter (6+ months), Crawler (8+ months), Crawler 10+(10+ months), Toddler (12+ months) and Preschooler (24+ months). Of course, the skilled artisan will appreciate, however, that the present models may be used with respect to any food products and is not limited to Applicant's portfolio.

TABLE 1

Developmental Milestones/Stages

|  | Birth+ (e.g., 0-4 mos.) | Supported Sitter (e.g., 4-6 mos.) | Sitter (e.g., 6+ mos.) |
|---|---|---|---|
| Gross Motor Development | Little truncal (vertical) stability | Controls the head Truncal stability to sit with support | Sits independently Truncal stability |
| Fine Motor Development | Reflexive grasp only | Sustained voluntary grasp | Primitive squeeze/ Palmar grasp Begins to rake (with fingers) food toward self |
| Oral Motor Development | Rooting and sucking Early gag reflex | Moves puree food forward and back with tongue to swallow Loss of extrusor reflex (tongue thrust) Gag reflex locus moves from the mid portion to the posterior of the tongue | Develops tongue wave and lip close Begins chewing movements using up and down movement of jaw ("munching") Uses upper lip to help clear food off of spoon Able to keep thicker purees in mouth Can drink from a cup hel |
| Cognitive Development | Enjoys bold colors Prefers looking at people Smiles, frowns, grimaces | Indicates an appetite for satiety Moves head forward to reach spoon when hungry or away when full | Reaches for food or spoon when hungry Slows down eating when full Clenches mouth shut when full |
| Appropriate Products | Breast milk Iron fortified formula | Breast milk Iron fortified single grain infant formula Single ingredient pureed foods | Breast milk Single or mixed grain iron fortified infant cereal Pureed foods Pureed meats Yogurt Fruit juice |
|  | Crawler (e.g., 8+ mos.) | Toddler (e.g., 12+ mos.) | Preschooler (e.g., 24+ mos.) |
| Gross Motor Development | Crawls with stomach off the floor May pull self to stand | Stands alone Walks with and without support | Runs well without falling Sits in a booster seat or at table |

TABLE 1-continued

Developmental Milestones/Stages

| | | | |
|---|---|---|---|
| Fine Motor Development | Struggles to get object out of reach<br>Begins to self-feed Finger Foods as pincer grasp is developing<br>Begins to manipulate objects correctly (spoon) but does not use it for self feeding yet<br>Explores objects with hands and mouth<br>Can hold lidded up indepen | Feeds self easily with fingers<br>Fine Pincer Grasp developed<br>Begins to use spoon and fork | Manipulates small objects<br>Practicing/mastering utensils<br>Eats/drinks with minimal spilling Holds and drinks from a cup |
| Oral Motor Development | Developing tongue lateralization used to move food to jaw line for mashing and chewing<br>Begins to use jaw to mash and chew food<br>Begins to track and sort pieces of food in the mouth | Able to drink from a cup or straw<br>Skillful at chewing of complex foods<br>Bites through a variety of textures<br>Coordinated tongue movement<br>First year molars begin erupting | Refined drinking skills<br>Chews skillfully and efficiently<br>Needs less time and fewer chews to finish a mouth full of food<br>Molars present<br>Uses tongue to clear food from lips |
| Cognitive Development | Reaches for food when hungry<br>Shows excitement for food when hungry<br>Shakes head to say "no more" when full | Rejection of new foods<br>Expresses desire for specific foods<br>Follows one step commands<br>Plays with food and throws it when full<br>Uses words like "all done"<br>Can lead parent by pointing | Follows simple instructions<br>Begins to sort by shape and color<br>Growing independence<br>Cautious about new foods<br>Prefers familiar foods |
| Appropriate Products | Breast milk<br>Cereal snacks<br>Single or mixed grain iron fortified infant cereal<br>Zweiback<br>Pureed/mashed foods<br>Pureed/mashed meats<br>Yogurt and dairy snacks<br>Fruit juice, iced fruits and vegetables | Whole 2% milk<br>Cereal<br>Table foods<br>Diced meats, legumes, vegetables, fruits<br>Yogurt and dairy snacks<br>Toddler meals | Whole 2% milk<br>Cereal<br>Table foods<br>Diced meats, legumes, vegetables, fruits<br>Yogurt and dairy snacks<br>Toddler meals |

Previously, the classification of age or stage was obtained subjectively or was based on food safety criteria once the food was commercialized. With the present models, however, the classification can be directed during early product development. These models have generated the understanding of what key texture attributes differentiate appropriate products across developmental stages. The purpose of the present disclosure was to identify driving texture attributes that contribute to the "staging" of current child-related food products and, thus, to create a method by which these attributes can be measured and then used to predict the appropriate age and staging of new innovation food products.

There are currently no consumer communications which give an explanation of the sensory descriptive and inherent analytical properties of each food "texture" that is developmentally appropriate for babies and young children based on oral and fine motor feeding skills being developed. Currently, parents use a trial and error approach when feeding their child, often resulting in unpleasant and unsuccessful mealtimes. The long term results of unsuccessful feeding may include delayed oral motor skills, picky eating habits, and gagging/choking. Age and developmental appropriateness may seem obvious to parents and medical professionals, however, the interaction of foods with different physical properties with the developmental skills (e.g., oral, fine and gross motor) of the child lead to the uniqueness of the presently disclosed methods and processes. Examples of this include, but are not limited to: (i) it is not a direct transition from smaller size piece to larger size pieces—in some cases, a larger sized product can be introduced at an earlier stage than a smaller, product with a different texture (e.g., Zwieback Toast versus Cinnamon Animal Graham); (ii) the child's ability to handle pieces in sauce is related to the thickness of the sauce/puree with thicker sauces holding pieces together to move as a cohesive mass in the mouth (e.g., "Thick Mash w/Lumps," Crawler stage) and thin sauces, which allow pieces to separate out leading to children gagging on these pieces; and (iii) major competitors of Applicant in the United States cluster all of the snack foods in the same stage 12+ month age group instead of distinguishing each according to developmental appropriateness by stage. Accordingly, the quantification of the texture attributes throughout Applicant's portfolio has created a texture fingerprint of each stage that can be shared with consumers to assist in transitioning children from breast milk or formula to pureed baby food and then to solid table foods.

To begin identification of driving texture attributes, Applicant collected sensory descriptive analysis, analytical measures, and product specification values to fingerprint the texture of about 36 food products currently marketed by Applicant that have a long and successfully history within the United States marketplace. The sensory descriptive analysis was performed by an expert panel trained in describing textural attributes of food products when placed in the mouth. Each panelist performed multiple iterations of analysis on the same food product and recorded a value for many different textural attributes of the food product. This data was used to identify approximately 22 texture attributes that distinguish products between each SHSH Milestone Stage. For example, Applicant identified which texture attributes vary in magnitude between the Crawler and Toddler stages. Accordingly, a specialized group of people specifically trained to evaluate characteristics of food with their mouth as an analytical instrument were used to obtain a first large group of data characterizing specific children's food products. Additionally, the data compiled by the expert panel can be continuously updated and refined to provide a comprehensive database of information to provide ever-improving predictions and classifications for children's food products.

Examples of the 22 identified texture attributes include, for example, amount of pieces in matrix, surface roughness, firmness, moistness, breakdown, cohesiveness of the mass, adhesiveness of the mass, moisture absorption, number of manipulations (to prepare to swallow), ease of swallow, residual mouthcoating, denseness, fracturability, and roughness of the mass. From these 22 texture attributes, statistical analysis (e.g., stepwise liner regression analysis or stepwise discriminant analysis) was used to determine driving, or key, texture attributes that had the most impact on age- or stage-classification of children's food products. These driving textures were also used to create mathematical models, which has the ability to predict appropriate age and stage positioning of newly invented products for infants and children (e.g., ages 0-48 months).

Examples of driving texture attributes for snacks (determined using stepwise linear regression analysis) include, for example, ease of swallow, residual mouthcoating, firmness and breakdown. Since a detailed analysis was performed by the expert panel, it is possible to associate ranges of numerical values (on a 100 point scale) for each of the driving texture attributes with respect to developmental stages of a child. For example, ranges for driving texture attributes of snack products are set forth below in Table 2.

TABLE 2

Examples of Driving Texture Attributes for Snack Food Products

| | Crawler | Crawler 10+ | Toddler | Preschooler |
|---|---|---|---|---|
| Ease of Swallow | 15-20 | 20-25 | 20-65 | >60 |
| Residual Mouthcoating | 10-25 | 10-30 | 10-30 | 10-25 |
| Firmness | 40-70 | 60-70 | 40-70 | 40-70 |
| Breakdown | >80 | 70-80 | 60-80 | 40-60 |

Examples of driving texture attributes for meals (determined using stepwise discriminant analysis) include, for example, moistness, ease of swallow and denseness. Again, since a detailed analysis was performed by the expert panel, it is possible to associate ranges of numerical values (on a 100 point scale) for each of the driving texture attributes with respect to developmental stages of a child. For example, ranges for driving texture attributes of snack products are set forth below in Table 3.

TABLE 3

Examples of Driving Texture Attributes for Meal Food Products

| | Supported Sitter | Sitter | Crawler | Crawler 10+ | Toddler | Preschooler |
|---|---|---|---|---|---|---|
| Moistness | >70 | >70 | >60 | >60 | >50 | >50 |
| Ease of Swallow | 0-10 | 0-10 | 10-25 | 10-25 | 20-60 | >75 |
| Denseness | 0-15 | 10-20 | 25-40 | 25-40 | 35-50 | >50 |

In addition to the expert panel analysis, Applicant also performed in-house analysis to characterize different attributes of the same 36 food products evaluated by the expert panel. Specifically, Applicant used a machine that simulates the mechanics inside the mouth to evaluate parameters such as, for example, force (N), work (N mm), slope (N/mm), length (mm), width (mm), thickness (mm), moisture (%), and Bostwick. These parameters may be included as additional textural attributes in the statistical analysis described herein below that aid in predicting and/or classifying food products. Applicant also confirmed reliability of the results obtained from the expert panel using Biplot and Clustering analysis. The Biplots indicated that product and panelist effect and their interaction was significant throughout; and discriminability, reproducibility, and scale were okay. K-means clustering also demonstrated reliability of the raw data.

The combination of the raw data obtained from the expert panel and the measurements obtained by Applicant was evaluated using statistical techniques to obtain the present models. During statistical analysis it was determined that the descriptive attributes of the 36 products evaluated by the expert panel would best be modeled most efficiently by separating the 36 products into snack and meal food products. Accordingly, different models were created for the 16 snack food products and the 20 meal food products. Additionally, the snack food products and meal food products were both evaluated with respect to age-appropriateness and developmental stage-appropriateness.

In an embodiment, stepwise regression analysis was used to develop mathematical models to predict minimum ages at which children should be provided with certain snack food products and meal food products. Based on expert panel analysis and in-house testing performed by Applicant, it was determined that the minimum age at which a child should consume a specific snack food product is best predicted by the driving texture attributes of i) firmness (evaluated by the Chewing Method) and ii) breakdown (evaluated by the Chewing Method). The Chewing Method consisted of compressing and chewing the sample with the molars. The primary parameters assessed in the Chewing Method included, but was not limited to, first bite with molars, first chew with molars, and chewing the sample 5-7 times with molars. A Multiple Regression Model of Age for Snacks with Predictions found that the minimum age can be calculated using the following formula:

Age (months)=78.5−1.4*(firmness (first bite))−0.4*(breakdown (chew))+0.0123*(firmness (first bite)).

Additionally, based on expert panel analysis and in-house testing performed by Applicant, and using stepwise regression analysis, it was determined that the minimum age at which a child should consume a specific meal food product is best predicted by the driving texture attributes of i) residual mouthcoating (evaluated by the Tongue to Palate Method) and ii) roughness of mass (evaluated by the Chewing Method). The Tongue to Palate Method consisted of compressing and manipulating the sample with the tongue against the hard palate. The primary parameters assessed in the Tongue to Palate Method included, but was not limited to, initial tongue manipulation, first compression with tongue to palate, manipulation of the sample 5-7 times with the tongue against the palate, and number of manipulations with the tongue. A Multiple Regression Model of Age for Meals with Predictions found that the minimum age can be calculated using the following formula:

$$\text{Age (months)}=1.9-0.16*(\text{residual mouthcoating (tongue)})+0.60*(\text{roughness of mass (chew)}).$$

In the present disclosure, discriminant analysis was used to develop mathematical models to predict developmental stages at which children should be provided with certain snack food products and meal food products. Specifically, based on the expert panel analysis and in-house testing performed by Applicant, it was determined that the developmental stage at which a child should consume a specific snack food product is best predicted by the driving texture attributes of i) firmness (evaluated by the Chewing Method); ii) breakdown (evaluated by the Chewing Method); iii) ease of swallow (evaluated by the Tongue to Palate Method); and iv) residual mouthcoating (evaluated by the Tongue to Palate Method). The Tongue to Palate Method and the Chewing Method are described herein above.

Additionally, based on the expert panel analysis and in-house testing performed by Applicant, it was determined that the developmental stage at which a child should consume a specific meal food product is best predicted by the driving texture attributes of i) moistness (evaluated by the Tongue to Palate Method); ii) ease of swallow (evaluated by the Tongue to Palate Method); and iii) denseness (evaluated by the Chewing Method). The Tongue to Palate Method and the Chewing Method are described herein above.

Due to the complexities of discriminant analysis, one specific formula for predicting and/or classifying food products with respect to developmental stage cannot be obtained, as is the case with the stepwise regression analysis used to predict and/or classify food product with respect to a minimum age. Indeed, the ever changing database of textural attributes for food groups would result in an ever changing covariance. For example, the end product from the expert panel's evaluation of the 36 food products was a large group of numerical values for each texture attribute evaluated for a plurality of food products. The large group of numerical values, texture attributes and identification of each of the plurality of food products may be stored in a database. As new food products are evaluated and added to the database, the models presented herein will change, thereby refining the models. Since the database of information is used as a source in the discriminant analysis evaluation, and the database is ever changing, it is not possible to use just one formula to predict and/or classify food products with respect to appropriate developmental stages. The skilled artisan will appreciate, however, how to perform discriminant analysis when provided with appropriate data.

In an embodiment, discriminant analysis may be most efficiently performed using a computer and a computer readable medium containing the necessary data and instructions for using a computer running appropriate software to perform the discriminant analysis. The necessary data may include, but is not limited to: (i) textural attributes including, for example, amount of pieces in matrix, surface roughness, firmness, moistness, breakdown, cohesiveness of the mass, adhesiveness of the mass, moisture absorption, number of manipulations (to prepare to swallow), ease of swallow, residual mouthcoating, denseness, fracturability, roughness of the mass, force (N), work (N mm), slope (N/mm), length (mm), width (mm), thickness (mm), moisture (%), and Bostwick; (ii) driving, or key, texture attributes including, for example, firmness (as analyzed by a first bite of the Chewing Method), breakdown (as analyzed by the Chewing Method), ease of swallow (as analyzed by the Tongue to Palate Method), residual mouthcoating (as analyzed by the Tongue to Palate Method), roughness of the mass (as analyzed by the Chewing Method), moistness (as analyzed by the Tongue to Palate Method), and denseness (as analyzed by the Chewing Method); and (iii) numerical values for the driving, or key, texture attributes for a newly developed food product for which prediction and/or classification is being sought.

The computer readable medium should also include code, or instructions, to instruct the computer processor how to perform discriminant analysis. The code interacts with the necessary data to predict and/or classify food products with respect to age- and/or stage-appropriateness for children. Once the analysis is performed, the code can also instruct the computer process how to format the output probabilities that the newly developed food products should be classified in a specific developmental stage. For example, if a new food product is being evaluated for prediction as, and/or classification into, a developmental stage selected from Supported Sitter, Sitter, Crawler, Crawler 10+, Toddler and Pre-schooler, the output of the discriminant analysis may indicate that the newly developed food product has a 29% probability of being classified as a Supported Sitter and a 71% probability of being classified as a Sitter. The skilled artisan will appreciate that any of the statistical analyses (e.g., regression, discriminant, etc.) or calculations discussed herein may be performed using a computer running appropriate software.

Applicant validated the models by evaluating several newly developed products using the models. Initially, Applicant obtained minimum age and stage information from an outside analytics company specializing in texture description of food products. Based on this information, Applicant used the newly developed models to also predict a minimum age for the newly developed products, as well as an appropriate developmental stage for same. The regression analysis models showed good correlation between the actual minimum age and the predicted minimum age for both snack and meal food products. Similarly, the discriminant analysis models achieved about 81% correct classification of stages for snack food products, and about 85% correct classification of stages for meal food products.

The previously identified driving texture attributes can be measured in new product prototypes and then compared to current products with strong in-market performance within the SHSH Milestone system through use of the validated mathematical model. In this regard, Applicant can use the present models to screen and train an in-house independent texture assessing panel, which will allow for measurement of texture attributes of new prototypes. This is, of course, appealing from a business perspective because Applicant will have greater reliability and confidence in age- and/or stage-classification of newly developed products earlier in the development process. As mentioned above, model validation and enhancements may be ongoing as full descriptive analysis is completed on newly developed textures.

The creation of the present models also provides for the systematic training of a larger panel of people to objectively rate texture attributes that can then be used to predict age and stage as well as guide further development. The models are also able to guide texture development of new food products for infants and children. The models may be used to guide development toward a target stage or directly suggest appropriate age or stage positioning for a new innovative product. If a specific positioning is desired, the texture attribute measures can be used to reformulate prototypes to match. For example, if a newly developed product is intended to be marketed as a Crawler food product, but in-house texture analysis using the present models indicates that the newly developed product is better suited for a Toddler food product, Applicant is able to reformulate the food product to achieve different texture attributes associated with a Crawler food product. Performing these assessments internally by Applicant instead of handing off the analysis to outside expert panels will also allow for time and cost savings.

The present disclosure also provided for the use of any of the above mentioned models and methods for the preparation of, modification of, design of, sale of, offer for sale of, and marketing of any products that results from use of same. For example, in an embodiment, new food products that have been modified or designed using a method for evaluating at least two texture attributes of the product are provided. The method includes evaluating at least two texture attributes of each of a plurality of known food products to obtain a numerical value for each texture attribute of each of the plurality of known food products, characterizing each of the plurality of known food products according to an appropriate age and an appropriate developmental stage for a child to consume the known food products, preparing a collection of information containing the plurality of known food products, the appropriate age for each known food product, the appropriate developmental stage for each known food product, and the texture attribute numerical values for each known food product, evaluating at least two texture attributes of a new food product to obtain a numerical value for each texture attribute, and using a computer running appropriate software to perform regression analysis using the collection of information to predict an appropriate age for the new food product. The method further includes modifying or designing the new food product according to the predicted appropriate age.

In summary, the methods of the present disclosure provide several advantages over known food prediction and classification methods. For example, benefits include, but are not limited to, using trained expert panelist to obtain texture descriptions for texture profiling of a large number of food products, development of a large-scale texture description database that can be used as a future resource for prediction, classification, training, etc., and the ability to compare texture attributes of newly developed food products to the texture attributes of food products already classified in the texture description database for efficient product development and reliable product classification/prediction. Benefits further include, but are not limited to use of the texture description database and presently developed models to determine driving texture attributes associated with different developmental stages, and the ability to constantly refine the present models to make future food predictions/classification even more reliable. Additionally, the methods of the present disclosure can be used to train in-house expert panels to help reduce development time and costs, as well as to increase product development efficiency.

By way of example and not limitation, the following examples are illustrative of various embodiments of the present disclosure.

Example 1

Process for Development and Validation of the Present Mathematical Models

1. Descriptive Analysis by Food Texture Experts

Applicant outsourced analysis of 36 children's food products currently marketed by Applicant to an outside consulting company specializing, in part, in food texture analysis. The company determined texture profiles of the 36 products using two methods of evaluation: Tongue to Palate and Chewing. The Tongue to Palate Method consisted of compressing and manipulating the sample with the tongue against the hard palate. The primary parameters assessed in the Tongue to Palate Method included, but was not limited to, initial tongue manipulation, first compression with tongue to palate, manipulation of the sample 5-7 times with the tongue against the palate, and number of manipulations with the tongue. The Chewing Method consisted of compressing and chewing the sample with the molars. The primary parameters assessed in the Chewing Method included, but was not limited to, first bite with molars, first chew with molars, and chewing the sample 5-7 times with molars. Eleven trained panelists performed three replicate evaluations of the 36 products for a total of 33 evaluations per product.

All 36 products were evaluated with respect to a core set of 22 descriptive attributes using the two methods of evaluation. The Tongue to Palate Method included 11 descriptive attributes including amount of pieces in matrix (described by an initial tongue manipulation), surface roughness, firmness, and moistness (described by the first compression with tongue to palate), breakdown, cohesiveness of mass, adhesiveness of mass, and moisture absorption (described by manipulation of the sample 5-7 times with the tongue against the palate), and number of manipulations to prepare to swallow, ease of swallow, and residual mouthcoating (described by the number of manipulations with tongue). The Chewing Method included 11 descriptive attributes including firmness (described by a first bite with molars), denseness, moistness, and fracturability (described by a first chew with molars), moisture absorption, breakdown, roughness of mass, cohesiveness of mass, and adhesiveness of mass (described by chewing of the sample 5-7 times with molars), and ease of swallow, and residual mouthcoating (described by a number of chews with molars).

Panelists evaluated all descriptive attributes on 100-point unstructured line scales, with the exception of the attribute number of manipulations to prepare to swallow. Panelists were instructed to enter numeric values for number of manipulations to prepare the sample to swallow. If the sample could not be swallowed after 50 manipulations with the tongue, panelists were instructed to stop the evaluation and enter a numeric value of 50.

A modified Williams design was utilized to serve samples in a balanced manner. Panelists cleansed their palates between samples with room temperature distilled water (approximately 72° F./22° C.). Samples were evaluated in individual computerized booths under white lights. All of the raw data collected during the evaluations was provided to Applicant for evaluation. Applicant analyzed the raw data to obtain mean scores for each descriptive/textural attribute for each food product.

2. Analytical Data Collected by Applicant

After completion of the texture descriptive study by the expert panel, Applicant performed several analytical tests on the 36 products. Using a PSM Pro machine, which mimics mechanics inside the mouth, Applicant was able to analyze each of the 36 products to obtain measurements for force (N), work (N mm), and slope (N/mm). Applicant also gathered additional data for the 36 products including, for example, length (mm), width (mm), thickness (mm), moisture (%), and Bostwick, where relevant. The combination of the raw data obtained by the expert panel and the measurements obtained by Applicant was sent to an outside statistics consulting company for evaluation.

3. Panel Performance Measured—Biplot and Cluster Analysis Performed

To evaluate the performance and reliability of the texture descriptive study performed by the expert panel, Applicant further evaluated the raw data obtained from the texture descriptive study. Specifically, Applicant prepared Biplot and Cluster graphs to verify reliability of the expert panel. The Biplots indicated that product and panelist effect and their interaction are significant throughout; and discriminability, reproducibility and scale use were okay. The k-means clustering also demonstrated reliability of the raw data.

4. Mathematical Model Created

The combination of the raw data obtained by the expert panel and the measurements obtained by Applicant was evaluated to obtain the present models. The raw data obtained by the expert panel and the measurements obtained by Applicant were related to a minimum age of a child using stepwise regression analysis. The raw data obtained by the expert panel and the measurements obtained by Applicant were related to a minimum developmental stage of a child using stepwise discriminant analysis. Separate analyses were performed for "snack" food products and "meal" food products.

Snack Food Products

Using statistical analysis, the textural attribute of breakdown (as described by the Chewing Method) was found to be the best single predictor of a minimum age at which children should consume a specific snack food product. Even more specifically, regression analysis determined that the minimum age at which a child should consume a specific snack food product is best predicted by the driving texture attributes of i) firmness (as described by a first bite using the Chewing Method) and ii) breakdown (as described by the Chewing Method). A Multiple Regression Model of Age for Snacks with Predictions found that the minimum age can be calculated using the following formula:

$$\text{Age (months)} = 78.5 - 1.4 \cdot (\text{firmness}) - 0.4 \cdot (\text{breakdown}) + 0.0123 \cdot (\text{firmness})^2.$$

A Discriminant Analysis Model for determining the most appropriate developmental stage at which a child should consume a snack food product was also successful. The discriminant analysis achieved about 81% correct classification rate of developmental stages using the driving texture attributes of firmness (as described by a first bite using the Chewing Method), and breakdown (as described by the Chewing Method).

Meal Food Products

Using statistical analysis, the textural attribute of roughness of mass (as described by the Chewing Method) was found to be the best single predictor of a minimum age at which children should consume a specific meal food product. Even more specifically, regression analysis determined that the minimum age at which a child should consume a specific meal food product is only marginally better predicted by the driving texture attributes of i) residual mouthcoating (as described by the Tongue to Palate Method) and ii) roughness of mass (as described by the Chewing Method). A Multiple Regression Model of Age for Meals with Predictions found that the minimum age can be calculated using the following formula:

$$\text{Age (months)} = 1.9 - 0.16 \cdot (\text{residual mouthcoating}) + 0.60 \cdot (\text{roughness of mass}).$$

A Discriminant Analysis Model for determining the most appropriate developmental stage at which a child should consume a meal food product was also successful. The discriminant analysis achieved about 90% correct classification rate of developmental stages using the driving texture attributes of firmness (as described by the Tongue to Palate Method), moistness (as described by the Tongue to Palate Method), ease of swallow (as described by the Tongue to Palate Method), denseness (as described by a first bite using the Chewing Method), and width (mm).

5. Mathematical Model Validated

To validate the statistical models for predicting the age- and stage-appropriateness of snacks and meals set forth above, five additional new products (three snacks and two meals) were added to the original 36 products (16 snacks and 20 meals) for evaluation. The original models for snacks involved only the driving texture attributes of firmness (as described by a first bite using the Chewing Method) and breakdown (as described using the Chewing Method). Since this data was available for the five new products, the original models were used in the validation. The original stage models for meals involved measurements for width (mm). Since width data was not available for the five new products, the stage model was refit based on the sensory attributes collected on the new meal products.

Snack Food Products

Regression analysis determined that the minimum age at which a child should consume a specific snack food product is best predicted by the driving texture attributes of i) firmness (as described by a first bite using the Chewing Method) and ii) breakdown (as described using the Chewing Method). A Multiple Regression Model of Age for Snacks with Predictions found that the minimum age can be calculated using the following formula:

$$\text{Age (months)} = 78.5 - 1.4 \cdot (\text{firmness}) - 0.4 \cdot (\text{breakdown}) + 0.0123 \cdot (\text{firmness})^2.$$

A Discriminant Analysis Model for determining the most appropriate developmental stage at which a child should consume a snack food product was also successful. The discriminant analysis achieved about 81% correct classification rate of developmental stages using the driving texture attributes of firmness (as described by a first bite using the Chewing Method) and breakdown (as described using the Chewing Method). Each of the three new snacks was strongly classified into the Crawler developmental stage.

Meal Food Products

Regression analysis determined that the minimum age at which a child should be provided with a specific meal food product is predicted by the driving texture attributes of i) residual mouthcoating (as described using the Tongue to Palate Method) and ii) roughness of mass (as described using the Chewing Method). A Multiple Regression Model of Age for Meals with Predictions found that the minimum age can be calculated using the following formula:

$$\text{Age (months)} = 2.45 - 0.11 \cdot (\text{residual mouthcoating}) + 0.50 \cdot (\text{roughness of mass}).$$

A "Sensory-Only" Discriminant Analysis Model for determining the most appropriate developmental stage at which a child should consume a meal food product was also successful. The discriminant analysis achieved about 85% correct classification rate of developmental stages using the texture attributes of moistness (as described using the Tongue to Palate Method), ease of swallow (as described using the Tongue to Palate Method), and denseness (as described by a first bite using the Chewing Method). One new food product was strongly classified into the Toddler developmental stage, while the other new food product was strongly classified into the Preschooler developmental stage.

As validation of the mathematical models, Applicant found that all four models (i.e., the regression model predicting the appropriate age for snacks, the discriminant model predicting the appropriate stage for snacks, the regression model predicting the appropriate age for meals, and the discriminant model predicting the appropriate stage for meals) fit the original data well. Additionally, the models were able to accurately predict the age and stage values of the five new products that were not included in the model-building analysis.

6. Develop Procedures for Training a Texture Panel

Based on the mathematical models presented in the present disclosure, Applicant believes it will now be easier to develop standard protocols for training an in-house expert texture panel that will be capable of easily and objectively predicting the minimum age and stage at which a child should consume a specific food product. Applicant will also be able to better adjust new food product formulations to develop food products for a specific minimum age or developmental stage of a child. For example, Applicant may use the above-mentioned mathematical models to classify a newly developed food product into a corresponding developmental stage (e.g., Crawler, Sitter, etc.). If the classification is not what Applicant had intended (e.g., the classification was Crawler, but Applicant intended to develop a new food product for a Sitter), Applicant will be able to adjust the formulation to achieve texture attributes that would classify the newly developed product as a Sitter product.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method for predicting an appropriate age at which a child should be provided with a new food product, the method comprising:
    evaluating at least two texture attributes of each of a plurality of known food products to obtain a numerical value for each texture attribute of each of the plurality of known food products;
    analyzing a firmness of the snack food product to obtain a firmness value;
    analyzing a breakdown of the snack food product to obtain a breakdown value;
    characterizing each of the plurality of known food products according to an appropriate age and an appropriate developmental stage for a child to consume the known food products;
    preparing a collection of information containing the plurality of known food products, the appropriate age for each known food product, the appropriate developmental stage for each known food product, and the textural attribute numerical values for each known food product;
    calculating the appropriate age of the child by inserting the firmness value and the breakdown value into a formula, the formula comprising:

$$age = 78.5 - 1.4*(\text{firmness value}) - 0.4*(\text{breakdown value}) + 0.0123*(\text{firmness value})2;$$

using a computer running appropriate software to perform regression analysis using the collection of information to predict an appropriate age for the new food product,
    wherein the at least two texture attributes are selected from the group consisting of amount of pieces in matrix, surface roughness, firmness, moistness, breakdown, cohesiveness of the mass, adhesiveness of the mass, moisture absorption, number of manipulations (to prepare to swallow), ease of swallow, residual mouthcoating, denseness, fracturability, roughness of the mass, force, work, and slope, length, width, thickness, moisture, Bostwick, and combinations thereof; and
    wherein the collection of information is a database.

2. The method according to claim 1 further comprising at least one of the steps of:
    a) determining driving texture attributes from the at least two evaluated texture attributes;
    b) performing statistical analysis on a first set of numerical values describing at least two texture attributes of each of a plurality of known food products;
    identifying at least two driving texture attributes that are good predictors of age from the at least two texture attributes, the at least two driving texture attributes selected from the group consisting of firmness, breakdown, residual mouthcoating, roughness of mass, and combinations thereof;
    evaluating the new food product to obtain a second set of numerical values describing the at least two driving texture attributes; and
    using a computer running appropriate software to perform regression analysis using the second set of numerical values to predict the appropriate age; or
    c) combinations thereof.

3. The method according to claim 1, wherein the evaluating is performed by at least one of:
    at least one person by placing the known food products in the person's mouth;
    at least one expert panel of at least two individuals;
    at least one machine; or
    combinations thereof.

4. The method according to claim 1, wherein the at least one known food products and the at least one new food product are at least one of: at least one children's food products; at least one snack food product; at least one food product that has been modified or designed; at least one meal food product; at least one food product that is being modified or designed to provide different texture attributes that relate to an older or younger appropriate age; a new food product that is being sold or offered for sale; a new food product that is being marketed; or combinations thereof.

5. The method according to claim 1, wherein the at least two texture attributes comprise firmness, moisture, breakdown, ease of swallow and residual mouthcoating.

6. The method according to claim 1, wherein method for predicting an appropriate age at which a child should be provided with a new food product is a method for predicting an appropriate developmental stage at which a child should be provided with a new food product.

7. The method according to claim 1, wherein method for predicting an appropriate age at which a child should be provided with a new food product is a method for classifying a new food product with respect to an appropriate age at which a child should be provided with the new food product.

8. The method according to claim 1, wherein method for predicting an appropriate age at which a child should be provided with a new food product is a method for predicting an appropriate age for a child to consume at least one new food product.

9. The method according to claim 1, wherein method for predicting an appropriate age at which a child should be provided with a new food product is a method for classifying a meal food product with respect to an appropriate age for a child to consume the food product.

10. The method according to claim 1, wherein method for predicting an appropriate age at which a child should be provided with a new food product is a method for reducing the risk of a child choking on a food product.

11. The method according to claim 1, comprising analyzing at least one of:
a firmness of the snack food product;
a breakdown of the snack food product;
analyzing a roughness of mass of the snack food product; or
combinations thereof;
is performed using a Chewing method.

12. The method according to claim 1, wherein the step of analyzing a firmness of the snack food product comprises at least two analysis of the food product to obtain first and second firmness values, and wherein the firmness value is an average of the first and second firmness values.

13. The method according to claim 1, wherein the step of analyzing a breakdown of the snack food product comprises at least two analysis of the food product to obtain first and second breakdown values, and wherein the breakdown value is an average of the first and second breakdown values.

14. A method for predicting an appropriate age at which a child should be provided with a new food product, the method comprising:
analyzing a residual mouthcoating of a meal food product to obtain a residual mouthcoating value;
analyzing a roughness of mass of the meal food product to obtain a roughness of mass value;
calculating the appropriate age of the child by inserting the residual mouthcoating value and the roughness of mass value into a formula, the formula comprising $$age=2.45-0.11*(\text{residual mouthcoating value})+0.50*(\text{roughness of mass value});$$

evaluating at least two texture attributes of each of a plurality of known food products to obtain a numerical value for each texture attribute of each of the plurality of known food products;
characterizing each of the plurality of known food products according to an appropriate age and an appropriate developmental stage for a child to consume the known food products;
preparing a collection of information containing the plurality of known food products, the appropriate age for each known food product, the appropriate developmental stage for each known food product, and the textural attribute numerical values for each known food product; and
using a computer running appropriate software to perform regression analysis using the collection of information to predict an appropriate age for the new food product, wherein the at least two texture attributes are selected from the group consisting of amount of pieces in matrix, surface roughness, firmness, moistness, breakdown, cohesiveness of the mass, adhesiveness of the mass, moisture absorption, number of manipulations (to prepare to swallow), ease of swallow, residual mouthcoating, denseness, fracturability, roughness of the mass, force, work, and slope, length, width, thickness, moisture, Bostwick, and combinations thereof; and
wherein the collection of information is a database.

15. The method according to claim 14, wherein the step of analyzing a residual mouthcoating of the meal food product is performed using a Tongue to Palate method.

16. The method according to claim 14, wherein the step of analyzing a residual mouthcoating of the meal food product comprises at least two analysis of the food product to obtain first and second residual mouthcoating values, and wherein the residual mouthcoating value is an average of the first and second residual mouthcoating values.

17. The method according to claim 14, wherein the step of analyzing a roughness of mass of the meal food product comprises at least two analysis of the food product to obtain first and second roughness of mass values, and wherein the roughness of mass value is an average of the first and second roughness of mass values.

18. A method for predicting an appropriate age at which a child should be provided with a new food product, the method comprising:
training an individual to predict an appropriate age for a child to consume a food product, the method comprising at least one of:
a) instructing the individual to analyze a residual mouthcoating of a meal food product to obtain a residual mouthcoating value;
instructing the individual to analyze a roughness of mass of the meal food product to obtain a roughness of mass value;
calculating the appropriate age of the child by inserting the residual mouthcoating value and the roughness of mass value into a formula, the formula comprising $$age=2.45-0.11*(\text{residual mouthcoating value})+0.50*(\text{roughness of mass value}); \text{ and}$$

comparing the calculated age to a known age;
b) instructing the individual to analyze a residual mouthcoating of the food product to obtain a residual mouthcoating value;
instructing the individual to analyze a roughness of mass of the meal food product to obtain a roughness of mass value;
calculating the appropriate age of the child by inserting the residual mouthcoating value and the roughness of mass value into a formula, the formula comprising $$age=2.45-0.11*(\text{residual mouthcoating value})+0.50*(\text{roughness of mass value}); \text{ and}$$

comparing the calculated age to a known age;
c) instructing the individual to analyze texture attributes of firmness, breakdown, ease of swallow and residual mouthcoating of a known food product;
providing a database comprising a plurality of known texture attribute values for each of a plurality of known food products, the database further comprising an appropriate developmental stage for each of the plurality of known food products, and the plurality of known food products including the known snack food product;
using a computer running appropriate software to perform discriminant analysis to determine probabilities of the known snack food product being classified into each of a plurality of development stages; and comparing the probabilities with the known appropriate developmental stage of the known snack food product;

d) instructing the individual to analyze texture attributes of moistness, ease of swallow and denseness of a known food product;

providing a database comprising a plurality of known texture attribute values for each of a plurality of known food products, the database further comprising an appropriate developmental stage for each of the plurality of known food products, and the plurality of known food products including the known meal food product;

using a computer running appropriate software to perform discriminant analysis to determine probabilities of the known meal food product being classified into each of a plurality of development stages;

comparing the probabilities with the known appropriate developmental stage of the known meal food product; or combinations thereof;

evaluating at least two texture attributes of each of a plurality of known food products to obtain a numerical value for each texture attribute of each of the plurality of known food products;

characterizing each of the plurality of known food products according to an appropriate age and an appropriate developmental stage for a child to consume the known food products;

preparing a collection of information containing the plurality of known food products, the appropriate age for each known food product, the appropriate developmental stage for each known food product, and the textural attribute numerical values for each known food product; and using a computer running appropriate software to perform regression analysis using the collection of information to predict an appropriate age for the new food product, wherein the at least two texture attributes are selected from the group consisting of amount of pieces in matrix, surface roughness, firmness, moistness, breakdown, cohesiveness of the mass, adhesiveness of the mass, moisture absorption, number of manipulations (to prepare to swallow), ease of swallow, residual mouthcoating, denseness, fracturability, roughness of the mass, force, work, and slope, length, width, thickness, moisture, Bostwick, and combinations thereof; and wherein the collection of information is a database.

19. A method for marketing a new food product, the method comprising:

modifying an existing food product or designing a new food product using a method for evaluating at least two texture attributes of the product, the method selected from the group consisting of those claimed in any one of claims 1-10 and claim 11; and marketing the new food product.

20. A method for selling or offering for sale a new food product, the method comprising:

preparing a new food product or modifying an existing food product using a method for evaluating at least two texture attributes of the product, the method selected from the group consisting of those claimed in any one of claims 1-10, and claims 11-18; and selling or offering for sale the new food product.

* * * * *